United States Patent [19]

Evans et al.

[11] Patent Number: 5,624,954
[45] Date of Patent: Apr. 29, 1997

[54] BENZO- AND PYRIDOPYRAN DERIVATIVES HAVING ANXIOLYTIC AND ANTI-CONVULSANT ACTIVITY

[75] Inventors: John M. Evans; Mervyn Thompson; Neil Upton, all of Essex, England

[73] Assignee: SmithKline Beecham p.l.c., England

[21] Appl. No.: 425,329

[22] Filed: Apr. 17, 1995

Related U.S. Application Data

[63] Continuation of Ser. No. 162,134, filed as PCT/GB92/01045 Jan. 11, 1992 published as WO92/22293 Dec. 23, 1992 abandoned.

[30] Foreign Application Priority Data

Jun. 13, 1991 [GB] United Kingdom ............ 9112721

[51] Int. Cl.$^6$ .................................................. A61K 31/35
[52] U.S. Cl. .......................................................... 514/456
[58] Field of Search ................. 514/456; 549/404, 549/399

[56] References Cited

U.S. PATENT DOCUMENTS 4,334,067  6/1982  Ohno et al. .

FOREIGN PATENT DOCUMENTS 0126311  11/1984  European Pat. Off. .
0205292  12/1986  European Pat. Off. .
0250077  12/1987  European Pat. Off. .
0370901  5/1990   European Pat. Off. .

*Primary Examiner*—Nicky Chan
*Attorney, Agent, or Firm*—Linda E. Hall; Stephen Venetianer; Edward T. Lentz

[57] ABSTRACT

4-(Fluorobenzoylamino)-3,4-dihydro-benzopyran derivatives are disclosed to possess anxiolytic and anti-convulsant activities.

8 Claims, No Drawings

BENZO- AND PYRIDOPYRAN DERIVATIVES HAVING ANXIOLYTIC AND ANTI-CONVULSANT ACTIVITY

This is a continuation of application Ser. No. 08/162,134, filed Dec. 13, 1993, now abandoned, which is a 371 of PCT/GB92/01045, filed Jun. 11, 1992.

This invention relates to a novel method of treatment and to novel compounds for use in such a method.

European Published Patent Application No. 0126311 discloses substituted benzopyran compounds having blood pressure lowering activity, including 6-acetyl-trans-4-(4-fluorobenzoylamino)-3,4-dihydro-2,2-dimethyl-2H-1-benzopyran-3-ol.

Also EP-A-0 376 524, EP-A-0 205 292, EP-A-0 250 077, EP-A-0 093 535, EP-A-0 150 202, EP-A-0 076 075 and WO0/89/05808 (Beecham Group plc) describe certain benzopyran derivatives which possess anti-hypertensive activity.

EP-A-0 350 805 (Biersdorf), EP-A-0 277 611, EP-A-0 277612, EP-A-0 337 179 and EP-A-0 355 565 (Hoechst Aktiengesellschaft); and EP-A-0 466 131 (Nissan Chemical Industries Ltd) also describe certain benzopyran derivatives which are believed to possess anti-hypertensive activity.

EP-A-0 430 621 and EP-A-0 385 584 (Beecham Group plc) describe the resolution of certain intermediates useful in the preparation of the compounds described in the above mentioned patent applications.

EP-A-0 194 885 (E. Lilly) describes certain amino substituted benzopyran derivatives possessing anti-convulsant activity.

It has now been surprisingly found that certain compounds of formula (I) possess anxiolytic and anti-convulsant activity, and are also believed to have utility in the treatment or prevention of mania, depression and the effects associated with withdrawal from substances of abuse.

Accordingly, the present invention provides a method of treatment and/or prophylaxis of anxiety and/or mania, and/or depression and/or the effects associated with withdrawal from substances of abuse such as cocaine, nicotine, alcohol and benzodiazepines, and/or disorders treatable and/or preventable with anti-convulsive agents, such as epilepsy, comprising administering to the sufferer in need thereof an effective or prophylactic amount of a compound of formula (I) or pharmaceutically acceptable salt thereof:

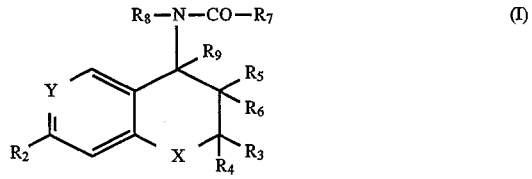

wherein:
either Y is N and $R_2$ is hydrogen, or Y is C—$R_1$
where:
either one of $R_1$ and $R_2$ is hydrogen and the other is selected from the class of hydrogen, $C_{3-8}$ cycloalkyl, $C_{1-6}$ alkyl optionally interrupted by oxygen or substituted by hydroxy, $C_{1-6}$ alkoxy or substituted aminocarbonyl, $C_{1-6}$ alkylcarbonyl, $C_{1-6}$ alkoxycarbonyl, $C_{1-6}$ alkylcarbonyloxy, $C_{1-6}$ alkoxy, nitro, cyano, halo, trifluoromethyl, $CF_3S$, or a group $CF_3$—A—, where A is —$CF_2$—, —CO—, —$CH_2$— or CH(OH), trifluoromethoxy, $C_{1-6}$ alkylsulphinyl, $C_{1-6}$ alkylsulphonyl, $C_{1-6}$ alkoxysulphinyl, $C_{1-6}$ alkoxysulphonyl, aryl, heteroaryl, arylcarbonyl, heteroarylcarbonyl, arylsulphinyl, heteroarylsulphinyl, arylsulphonyl, heteroarylsulphonyl in which any aromatic moiety is optionally substituted, $C_{1-6}$ alkylcarbonylamino, $C_{1-6}$ alkoxycarbonylamino, $C_{1-6}$ alkyl-thiocarbonyl, $C_{1-6}$ alkoxy-thiocarbonyl, $C_{1-6}$ alkyl-thiocarbonyloxy, 1-mercapto $C_{2-7}$ alkyl, formyl, or aminosulphinyl, aminosulphonyl or aminocarbonyl, any amino moiety being optionally substituted by one or two $C_{1-6}$ alkyl groups, or $C_{1-6}$ alkylsulphinylamino, $C_{1-6}$ alkylsulphonylamino, $C_{1-6}$ alkoxysulphinylamino or $C_{1-6}$ alkoxysulphonylamino, or ethylenyl terminally substituted by $C_{1-6}$ alkylcarbonyl, nitro or cyano, or —C($C_{1-6}$ alkyl)NOH or —C($C_{1-6}$ alkyl)NNH$_2$, or one of $R_1$ and $R_2$ is nitro, cyano or $C_{1-3}$ alkylcarbonyl and the other is methoxy or amino optionally substituted by one or two $C_{1-6}$ alkyl or by $C_{2-7}$ alkanoyl;
one of $R_3$ and $R_4$ is hydrogen or $C_{1-4}$ alkyl and the other is $C_{1-4}$ alkyl or $R_3$ and $R_4$ together are $C_{2-5}$ polymethylene;
$R_5$ is $C_{1-6}$ alkylcarbonyloxy, benzoyloxy, ONO$_2$, benzyloxy, phenyloxy or $C_{1-6}$ alkoxy and $R_6$ and $R_9$ are hydrogen or $R_5$ is hydroxy and $R_6$ is hydrogen or $C_{1-2}$ alkyl and $R_9$ is hydrogen;
$R_7$ is fluorophenyl;
$R_8$ is hydrogen or $C_{1-6}$ alkyl;
the $R_8$—N—CO—$R_7$ group being trans to the $R_5$ group;
and X is oxygen or NR$_{10}$ where $R_{10}$ is hydrogen or $C_{1-6}$ alkyl.

Compounds of formula (I) include those in which Y is C—$R_1$, where;
either one of $R_1$ and $R_2$ is hydrogen and the other is selected from the class of hydrogen, $C_{1-6}$ alkylcarbonyl, $C_{1-6}$ alkoxycarbonyl, $C_{1-6}$ alkylcarbonyloxy, $C_{1-6}$ alkylhydroxymethyl, nitro, cyano, chloro, trifluoromethyl, trifluoromethoxy, $C_{1-6}$ alkylsulphinyl, $C_{1-6}$ alkylsulphonyl, $C_{1-6}$ alkoxysulphinyl, $C_{1-6}$ alkoxysulphonyl, $C_{1-6}$ alkylcarbonylamino, $C_{1-6}$ alkoxycarbonylamino, $C_{1-6}$ alkyl-thiocarbonyl, $C_{1-6}$ alkoxy-thiocarbonyl, $C_{1-6}$ alkyl-thiocarbonyloxy, 1-mercapto $C_{2-7}$ alkyl, formyl, or aminosulphinyl, aminosulphonyl or aminocarbonyl, the amino moiety being optionally substituted by one or two $C_{1-6}$ alkyl groups, or $C_{1-6}$ alkylsulphinylamino, $C_{1-6}$ alkylsulphonylamino, $C_{1-6}$ alkoxysulphinylamino or $C_{1-6}$ alkoxysulphonylamino, or ethylenyl terminally substituted by $C_{1-6}$ alkylcarbonyl, nitro or cyano, or —C($C_{1-6}$ alkyl)NOH or —C($C_{1-6}$ alkyl)NNH$_2$, or one of $R_1$ and $R_2$ is nitro, cyano or $C_{1-3}$ alkylcarbonyl and the other is methoxy or amino optionally substituted by one or two $C_{1-6}$ alkyl or by $C_{2-7}$ alkanoyl;
one of $R_3$ and $R_4$ is hydrogen or $C_{1-4}$ alkyl and the other is $C_{1-4}$ alkyl or $R_3$ and $R_4$ together are $C_{2-5}$ polymethylene;
$R_5$ is hydroxy and $R_6$ is hydrogen;
$R_7$ is fluorophenyl;
$R_8$ is hydrogen or $C_{1-6}$ alkyl; and
$R_9$ is hydrogen;
the $R_8$—N—CO—$R_7$ group being trans to the $R_5$ group.

All $C_{1-6}$ alkyl or alkyl containing groups in formula (I) are preferably selected from methyl, ethyl, n- and iso-propyl, n-, iso-, sec- and tert-butyl.

Suitable $C_{3-8}$ cycloalkyl groups include cyclopropyl, cyclobutyl, cyclopentyl, cyclohexyl, cycloheptyl and cyclooctyl.

Aryl includes but is not limited to phenyl and naphthyl.

Heteroaryl includes a 5- or 6-membered monocyclic or 9- or 10-membered bicyclic of which 5- or 6-membered monocyclic heteroaryl is preferred. In addition, 5- or 6-membered monocyclic or 9- or 10-membered bicyclic heteroaryl preferably contains one, two or three heteroatoms which are selected from the class of oxygen, nitrogen and sulphur and which, in the case of there being more than one heteroatom, are the same or different. Examples of 5- or 6-membered monocyclic heteroaryl containing one, two or three heteroatoms which are selected from the class of oxygen, nitrogen and sulphur include furyl, thienyl, pyrryl, oxazolyl, thiazolyl, imi dazolyl and thiadiazolyl, and pyridyl, pyridazyl, pyrimidyl, pyrazolyl and triazolyl. Preferred examples of such groups include furanyl, thienyl, pyrryl and pyridyl, in particular 2- and 3-furyl, 2- and 3-pyrryl, 2- and 3-thienyl, and 2-, 3- and 4-pyridyl. Examples of 9- or 10-membered bicyclic heteroaryl containing one, two or three heteroatoms which are selected from the class of oxygen, nitrogen and sulphur include benzofuranyl, benzothienyl, indolyl and indazolyl, quinolyl and isoquinolyl, and quinazolyl. Preferred examples of such groups include 2- and 3-benzofuryl, 2- and 3-benzothienyl, and 2- and 3-indolyl, and 2- and 3-quinolyl.

Suitable examples of groups or atoms for optional substitution of aryl and heteroaryl include one, two or three substituents independently selected from $C_{1-4}$ alkyl, $C_{1-4}$ alkoxy, halo (such as fluoro, chloro, bromo), hydroxy, nitro, cyano and $SO_nH$, where n=0 to 2.

Preferably $R_2$ is hydrogen.

Examples of suitable $R_1$ substituents include cyano, methoxy, trifluoromethoxy, chloro, trifluoromethyl, ethylcarbonyl, acetyl, hydrogen, methyl, ethyl, iso-propyl, tertiary-butyl, nitro, $C_2F_5$, methoxycarbonyl, phenylsulphonyl, phenyl, fluoro, iodo, cyclopentyl, aminocarbonylmethyl and 1-hydroxyethyl. Preferably $R_1$ is cyano, acetyl or ethyl.

Preferably $R_3$ and $R_4$ are both methyl.

Preferably $R_5$ is hydroxy and $R_6$ and $R_9$ are hydrogen or $R_5$ is hydroxy, $R_6$ is $C_{1-2}$ alkyl and $R_9$ is hydrogen, more preferably $R_5$ is hydroxy and $R_6$ and $R_9$ are hydrogen.

It should be appreciated that the term fluorophenyl relating to $R_7$ encompasses phenyl which has 1,2,3,4 or 5 fluoro groups attached to the phenyl ring. Preferably there are 1 or 2 fluoro groups attached to the phenyl ring and most preferably there is 1 fluoro group attached to the ring.

The fluoro group or groups may be in any position around the phenyl ring, preferably in the case of mono fluorophenyl the fluoro is in the 3 or 4 position.

In the case of difluorophenyl, preferably the fluoro substituents are at positions 2,4 or 3,4.

Preferably $R_8$ is hydrogen or $C_{1-4}$ alkyl, more preferably $R_8$ is hydrogen, methyl or ethyl.

Preferably X is oxygen.

It should be appreciated that the compounds of formula (I) may have chiral carbon atoms at positions 2, 3 and 4 and therefore may exist as enantiomers. The present invention extends to each enantiomer and to mixtures thereof including racemates. Preferably the compounds of formula (I) exist as 4S, 3R enantiomers.

It should also be appreciated that certain $R_1$ substituents also have chiral centres and therefore may exist as enantiomers. The present invention extends to each enantiomer and to mixtures thereof including racemates An example of a compound of formula (I) is trans-6-acetyl-4(4-fluorobenzoylamino )-3,4-dihydro-2,2-dimethyl-2H-1-benzopyran-3-ol (compound X).

The following novel compounds of formula (I) also form an aspect of the present invention, (herein referred to as compounds of formula (I')):

trans-6-Cyano-3,4-dihydro-2,2-dimethyl-4-(4-fluorobenzoylamino)2H-1-benzopyran-3-ol, (Example 5), trans-6-Chloro-3,4-dihydro-2,2-dimethyl-4-(4-fluorobenzoylamino)2H-1-benzopyran-3-ol, (Example 6), trans-6-Trifluoromethyl-4-(4-fluorobenzoylamino )-3,4-dihydro-2,2-dimethyl-2H-1-benzopyran-3-ol, (Example 7), trans-6-Cyano-4-(4-fluorobenzoylmethylamino)-3,4-dihydro-2,2-dimethyl2H-1-benzopyran-3-ol, (Example 8), trans-6-Ethylcarbonyl-3,4-dihydro-2,2-dimethyl-4-(4fluorobenzoylamino)2H-1-benzopyran-3-ol, (Example 9), trans-6-Ethylcarbonyl-3,4-dihydro-2,2-dimethyl 4-(4-fluorobenzoylmethylamino)2H-1-benzopyran-3-ol, (Example 10), trans-6-Acetyl-4-(4-fluorobenzoylmethylamino)-3,4-dihydro-2,2-dimethyl-2H-1-benzopyran-3-ol, (Example 11), trans-6-Cyano-3,4-dihydro-4-(4-fluorobenzoylethylamino)-2,2-dimethyl-2H-1-benzopyran-3-ol (Example 12), trans-4-(4-Fluorobenzoylamino)-3,4-dihydro-2,2-dimethyl-7-nitro-2H-1-benzopyran-3-ol (Example 13), trans-6-Acetyl-4-(4-Fluorobenzoylamino)-3,4-dihydro-2,2-dimethyl-2H-1-benzopyran-3-ol (Example 18), trans-6-Acetyl-4R-(4-fluorobenzoylamino)-3,4-dihydro-2,2-dimethyl-2H-1-benzopyran-3S-ol (Example 19), trans-6-Acetyl-4S-(4-fluorobenzoylamino)-3,4-dihydro-2,2-dimethyl-2H-1-benzopyran-3R-ol (Example 20), trans-6-Cyano-4S-(4-fluorobenzoylamino)-3,4-dihydro-2,2-dimethyl-2H-1-benzopyran-3R-ol (Example 25), trans-6-Cyano-4-(4-fluorobenzoylamino)-3,4-dihydro-2,2,3-trimethyl-2H-1-benzopyran-3-ol (Example 26), trans-4-(4-Fluorobenzoylamino)-3,4-dihydro-2,2-dimethyl-6-nitro-2H-1-benzopyran-3-ol (Example 27), trans-4-(4-Fluorobenzoylamino)-3,4-dihydro-6-methoxycarbonyl-2,2-dimethyl-2H-1-benzopyran-3-ol (Example 30), trans-6-Fluoro-4-(4-fluorobenzoylamino)-3,4-dihydro-2,2-dimethyl-2H-1-benzopyran-3-ol (Example 34), trans-4-(4-fluorobenzoyl-methylamino)-6-trifluoromethyl-3,4-dihydro-2,2-dimethyl-2H-1-benzopyran-3-ol (Example 42), trans-4-(4-Fluorobenzoylamino)-3,4-dihydro-6-iodo-2,2-dimethyl-2H-1-benzopyran-3-ol (Example 47) and trans-6-Aminocarbonylmethyl-4-(4-fluorobenzoylamino) -3,4-dihydro-2,2-dimethyl-2H-1-benzopyran-3-ol (Example 49).

The administration to the mammal may be by way of oral or parenteral administration.

An amount effective to treat the disorders hereinbefore described depends on the usual factors such as the nature and severity of the disorders being treated and the weight of the mammal. However, a unit dose will normally contain 1 to 1000 mg, suitably 1 to 500 mg, for example an amount in the range of from 2 to 100 mg such as 2, 5, 10, 20, 30, 40, 50 and 100 mg of the active compound. Unit doses will normally be administered once or more than once per day, for example 2, 3, 4, 5 or 6 times a day, more usually 2 to 4 times a day, such that the total daily dose is normally in the range, for a 70 kg adult of 1 to 1000 mg, for example 50 to 500 mg, that is in the range of approximately 0.01 to 50 mg/kg/day, more usually 0.1 to 50 mg/kg/day, for example 1 to 50 mg/kg/day.

It is greatly preferred that the compound of formula (I) is administered in the form of a unit-dose composition, such as a unit dose oral, rectal, topical or parenteral (especially intravenous) composition.

Such compositions are prepared by admixture and are suitably adapted for oral or parenteral administration, and as such may be in the form of tablets, capsules, oral liquid preparations, powders, granules, lozenges, reconstitutable powders, injectable and infusable solutions or suspensions or suppositories. Orally administrable compositions are preferred, in particular shaped oral compositions, since they are more convenient for general use.

Tablets and capsules for oral administration are usually presented in a unit dose, and contain conventional excipients such as binding agents, fillers, diluents, tabletting agents, lubricants, disintegrants, colourants, fLavourings, and wetting agents. The tablets may be coated according to well known methods in the art.

Suitable fillers for use include cellulose, mannitol, lactose and other similar agents. Suitable disintegrants include starch, polyvinylpyrrolidone and starch derivatives such as sodium starch glycollate. Suitable lubricants include, for example, magnesium stearate. Suitable pharmaceutically acceptable wetting agents include sodium lauryl sulphate.

These solid oral compositions may be prepared by conventional methods of blending, filling, tabletting or the like. Repeated blending operations may be used to distribute the active agent throughout those compositions employing large quantities of fillers. Such operations are, of course, conventional in the art.

Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethyl cellulose, aluminium stearate gel or hydrogenated edible fats, emulsifying agents, for example lecithin, sorbitan monooleate, or acacia; non-aqueous vehicles (which may include edible oils), for example, almond oil, fractionated coconut oil, oily esters such as esters of glycerine, propylene glycol, or ethyl alcohol; preservatives, for example methyl or propyl p-hydroxybenzoate or sorbic acid, and if desired conventional flavouring or colouring agents.

Oral formulations also include conventional sustained release formulations, such as tablets or granules having an enteric coating.

For parenteral administration, fluid unit dose forms are prepared containing the compound and a sterile vehicle. The compound, depending on the vehicle and the concentration, can be either suspended or dissolved. Parenteral solutions are normally prepared by dissolving the compound in a vehicle, and filter sterilising before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the compound is suspended in the vehicle instead of being dissolved and sterilised by exposure to ethylene oxide before suspending in the sterile vehicle. Advantageously, a surfactant or wetting agent is included in the composition to facilitate uniform distribution of the compound of the invention.

As is common practice, the compositions will usually be accompanied by written or printed directions for use in the medical treatment concerned.

The present invention further provides a pharmaceutical composition for use in the treatment and/or prophylaxis of anxiety and/or mania and/or depression and/or the effects associated with withdrawal from substances of abuse such as cocaine, nicotine, alcohol and benzadiazepines and/or disorders treatable or preventable with anti-convulsive agents, such as epilepsy, which comprises a compound of formula (I), or a pharmaceutically acceptable salt thereof, in particular, compounds of examples 1 to 50, and a pharmaceutically acceptable carrier.

In a further aspect the invention provides the use of a compound of formula (I), or a pharmaceutically acceptable salt thereof, in particular compounds of examples 1 to 50 inclusive, for the manufacture of a medicament for the treatment and/or prophylaxis of anxiety and/or mania and/or depression and/or the effects associated with withdrawal from substances of abuse such as cocaine, nicotine, alcohol and benzadiazepines and/or disorders treatable or preventable with anti-convulsive agents, such as epilepsy.

Such compositions may be prepared in the manner as hereinbefore described.

The invention also provides novel compounds of formula (I) and pharmaceutically acceptable salts thereof wherein $R_7$ is 2- or 3-fluorophenyl, 2, 4- or 3,4- difluorophenyl. Such compounds will hereinafter be referred to as compounds of formula (Ia).

Examples of compounds of formula (Ia) include:

trans-6-Cyano-3,4-dihydro-2,2-dimethyl-4-(3-fluorobenzoylamino)2H-1-benzopyran-3-ol (Example 1), trans-6-Cyano-3,4-dihydro-2,2-dimethyl-4-(2-fluorobenzoylamino) 2H-1-benzopyran-3-ol (Example 2), trans-6-Trifluoromethoxy-3,4-dihydro-2,2-dimethyl-4-(3fluorobenzoylamino)2H-1-benzopyran-3-ol (Example 3), trans-6-Cyano-4S-(3-fluorobenzoylamino)-3,4-dihydro-2,2-dimethyl-2H-1-benzopyran-3R-ol (Example 21), trans-6-Cyano-4R-(3-fluorobenzoylamino)-3,4-dihydro-2,2-dimethyl-2H-1-benzopyran-3S-ol (Example 22), trans-6-Cyano-4S-(2-fluorobenzoylamino)-3,4-dihydro-2,2-dimethyl-2H-1-benzopyran-3R-ol (Example 24), trans-6-Cyano-4S-(2,4-difluorobenzoylamino)-3,4-dihydro-2,2-dimethyl-2H-1-benzopyran-3R-ol (Example 28), trans-6-Acetyl-4-(3-fluorobenzoylamino)-3,4-dihydro-2,2-dimethyl-2H-1-benzopyran-3-ol (Example 31), trans-4-(2-Fluorobenzoylamino)-3,4-dihydro-2,2-dimethyl-2H-pyrano[3,2c]pyridin-3-ol (Example 38), trans-4-(3-Fluorobenzoylamino)-3,4-dihydro-2,2-dimethyl-2H-pyrano[3, 2c]pyridin-3-ol (Example 39), trans-6-Cyano-4-(3,4-difluorbenzoyl-methylamino)-3,4-dihydro-2,2-dimethyl-2H-1-benzopyran-3-ol (Example 41) and trans-6-cyano-4S-(3,4-difluorobenzoylamino)-3,4-dihydro-2,2-dimethyl-2H-1-benzopyran-3R-ol (Example 44).

The invention further provides novel compounds of formula (I) and pharmaceutically acceptable salts thereof wherein Y is $CR_1$ where $R_1$ and $R_2$ are both hydrogen or one of $R_1$ and $R_2$ is trifluoromethoxy, $C_{1-6}$ alkyl optionally interrupted with oxygen or substituted with hydroxy, $C_{1-6}$ alkoxy or substituted amino-carbonyl, $CF_3A$—(where A is —$CF_2$—, —CO—, —$CH_2$) or CH(OH)), aryl sulphonyl, aryl $C_{3-8}$ cycloalkyl, $C_{1-6}$ alkoxy, heteroaryl, arylcarbonyl, heteroarylcarbonyl, arylsulphinyl, heteroarylsulphinyl, heteroarylsulphonyl, in which any aromatic moiety is optionally substituted and the other is hydrogen. Such compounds will hereinafter be referred to as compounds of formula (Ib).

Examples of compounds of formula (Ib) include:

trans-6-Trifluoromethoxy-3,4-dihydro-2,2-dimethyl-4-(3fluorobenzoylamino)2H-1-benzopyran-3-ol (Example 3), trans-3,4-Dihydro-2,2-dimethyl-4-(4-fluorobenzoylamino)-2H-1-benzopyran-3-ol (Example 4), trans-4-(4-Fluorobenzoylamino)-3,4-dihydro-2,2,6-trimethyl-2H-1-benzopyran-3-ol (Example 14), trans-6-Ethyl-4-(4-fluorobenzoylamino)-3,4-dihydro-2,2-dimethyl-2H-1-benzopyran-3-ol (Example 15), trans-6-Ethyl-4-(4-fluorobenzoylethylamino)-3,4-dihydro-2,2-dimethyl-2H1-benzopyran-3-ol (Example 16), trans-4-(4-Fluorobenzoylamino)-3,4-dihydro-2,2-dimethyl-6-isopropyl-2H1-benzopyran-3-ol (Example 17), trans-6-Ethyl-4-(4-fluorobenzoylmethylamino)-3,4-dihydro-2,2-dimethyl-2H-1-benzopyran-3-ol (Example 23), trans-4-(4-Fluorobenzoylamino)-6-pentafluoroethyl-3,4-dihydro-2,2-dimethyl-2H-1-benzopyran-3-ol (Example 29), trans-4-(4-Fluorobenzoylamino)-3,4-dihydro-2,2-dimethyl-6-phenylsulphonyl-2H-1-benzopyran-3-ol (Example 32), trans-4-(4-Fluorobenzoylamino)-3,4-dihydro-2,2-dimethyl-6-phenyl-2H-1-benzopyran-3-ol (Example 33), trans-6-Ethyl-4S-(4-fluorobenzoylamino)-3,4-dihydro-2,2-dimethyl-2H-1-benzopyran-3R-ol (Example 35), trans-4R-(4-Fluorobenzoylamino)-3,4-dihydro-6-(1-hydroxyethyl )-2,2-dimethyl-2H-1-benzopyran-3S-ol (Example 36), trans-4S-(4-Fluorobenzoylamino)-3,4-dihydro-6-(1-hydroxyethyl)-2,2-dimethyl-2H-1-benzopyran-3R-ol (Example 37), trans-4-(4-fluorobenzoyl-methylamino)-3,4-dihydro-2,2-dimethyl-2H-1-benzopyran-3-ol (Example 43), trans-6-t-Butyl-4-(4-Fluorobenzoylamino)-3,4-dihydro-2,2-dimethyl-2H-1-benzopyran-3-ol (Example 46), trans-4-(4-Fluorobenzoylamino)-3,4-dihydro-2,2-dimethyl-6-cyclopentyl-2H-1-benzopyran-3-ol (Example 48) and trans-4-(4-Fluorobenzoylamino)-3,4-dihydro-6-methoxy-2,2-dimethyl-2H1-benzopyran-3-ol (Example 50).

The present invention also provides novel compounds of formula (I) and pharmaceutically acceptable salts thereof, where Y is N and $R_2$ is hydrogen. Such compounds will hereinafter be referred to as compounds of formula (Ic).

Examples of compounds of formula (Ic) include:

trans-4-(2-Fluorobenzoylamino)-3,4-dihydro-2,2-dimethyl-2H-pyrano[3,2-c]pyridin-3-ol (Example 38), trans-4-(3-Fluorobenzoylamino)-3,4-dihydro-2,2-dimethyl-2H-pyrano[3,2-c]pyridin-3-ol (Example 39) and trans-4-(4-Fluorobenzoylamino)-3,4-dihydro-2,2-dimethyl-2H-pyrano[3,2-c]pyridin-3-ol (Example 40).

The present invention also provides novel compounds of formula (I) and pharmaceutically acceptable salts thereof, where X is $NR_{10}$ where $R_{10}$ is hydrogen or $C_{1-6}$ alkyl. Such compounds will hereinafter be referred to as compounds of formula (Id).

An example of a compound of formula (Id) is:

trans-6-Cyano-4-(4-fluorobenzoylamino)-2,2-dimethyl-1,2,3,4-tetrahydroquinolin-3-ol (Example 45).

Generally, compounds of formula (I) may be prepared by procedures generally described or analogous to those described in EP-0126311, EP-0376524, EP-205292, EP-0250077, EP-0093535, EP-0150202, EP-0076075, WO/89/05808, EP-0350805, EP-0277611, EP-0277612, EP-0337179, EP-0355565 and EP-0466131.

The invention also provides a process for the preparation of novel compounds of formula (I') or pharmaceutically acceptable salts thereof, which comprises acylating a compound of formula (II'):

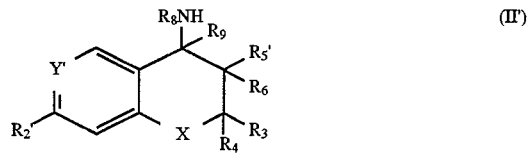

(II')

wherein Y', $R_2$' and $R_5$' are the required variables Y, $R_2$ or $R_5$ as defined in formula (I) or a group convertible thereto and $R_3$, $R_4$, $R_6$, $R_8$, $R_9$ and X are the required variables as defined in formula (I), the $R_8$NH group being trans to the $R_5$ group, with and acylating agent of formula (IIIb):

$R_7COL_1$ where $R_7$ is as required and as defined in formula (I) and $L_1$ is a leaving group; thereafter optionally or as necessary and in any appropriate order convening any $R_1$', $R_2$' and $R_5$' groups to $R_1$, $R_2$ and $R_5$ respectively, interconverting $R_8$ when hydrogen to $C_{1-6}$ alkyl, separating any enantiomers and forming a pharmaceutically acceptable salt or solvate.

In particular, the present invention also provides a process for the preparation of compounds of formula (Ia), or a pharmaceutically acceptable salt thereof, which comprises acylating a compound of formula (IIa):

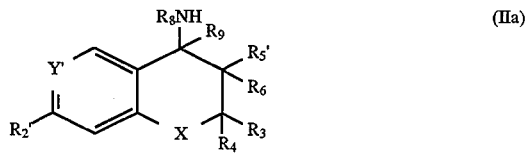

(IIa)

wherein Y', $R_2$' and $R_5$' are Y, $R_2$ or $R_5$ as defined in formula (I) or a group convertible thereto and $R_3$, $R_4$, $R_6$, $R_8$, $R_9$ and X are as defined in formula (I), the $R_8$NH group being trans to the $R_5$' group, with an acylating agent of formula (IIIa):

(IIIa)

where $R_7{}^a$ is 2- or 3-fluorophenyl or 2,4-or 3,4-difluorophenyl and $L_1$ is a leaving group; thereafter optionally or as necessary and in any appropriate order converting any Y', $R_2'$ or $R_5'$ group to Y, $R_2$ or $R_5$ respectively, interconverting $R_8$ when hydrogen to $C_{1-6}$ alkyl, separating any entantioners and forming a pharmaceutically acceptable salt or solvate.

The present invention also provides a process for the preparation of compounds of formula (Ib), or a pharmaceutically acceptable salt thereof, which comprises acylating a compound of formula (IIb):

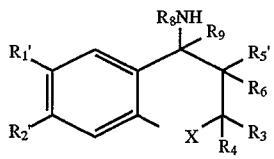
(IIb)

where $R_1'$ and $R_2'$ are both hydrogen or one of $R_1$ and $R_2$ is trifluoromethoxy, $C_{1-6}$ alkyl optionally interrupted with oxygen or substituted with hydroxy, $C_{1-6}$ alkoxy or substituted aminocarbonyl, $CF_3A$— (where A is $CF_2$, —CO—, —$CH_2$— or CH(OH)), aryl, aryl sulphonyl, aryl $C_{3-8}$ cycloalkyl, $C_{1-6}$ alkoxy, heteroaryl, arylcarbonyl, heteroarylcarbonyl, arylsulphinyl, heteroarylsulphinyl, heteroarylsulphonyl, in which any aromatic moiety is optionally substituted and the other is hydrogen, or groups convertible to any of these; $R_5'$ is $R_5$ as defined in formula (I) or a group convertible thereto and $R_3$, $R_4$, $R_6$, $R_8$, $R_9$ and X are as defined in formula (I) the $R_8$NH group being trans to the $R_5'$ group, with a compound of formula (IIIb):

$R_7COL_1$  (IIIb)

where $R_7$ is as defined in formula (I) and $L_1$ is a leaving group; thereafter optionally or as necessary and in any appropriate order converting any $R_1'$, $R_2'$ and $R_5'$ groups to $R_1$, $R_2$ and $R_5$ respectively, interconverting $R_8$ when hydrogen to $C_{1-6}$ alkyl, separating any enantiomers and forming a pharmaceutically acceptable salt or solvate.

The present invention also provides a process for the preparation of compounds of formula (Ic), or a pharmaceutically acceptable salt thereof, which comprises acylating a compound of formula (IIc):

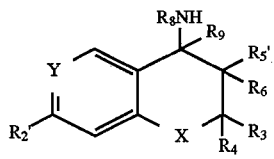
(IIc)

in which Y is N, $R_5'$ is $R_5$, as defined in relation to formula (I) or a group convertible to $R_5$ and $R_2'$ is hydrogen or a group convertible thereto, $R_6$, $R_3$, $R_4$, $R_8$, $R_9$ and X are as defined in formula (I), the $R_8$NH group being trans to the $R_5'$ group, with an acylating agent of formula (IIIb):

$R_7COL_1$  (IIIb)

where $R_7$ is as defined in formula (I) and $L_1$ is a leaving group; thereafter optionally or as necessary and in any appropriate order converting any $R_2'$ or $R_5'$ group to hydrogen or $R_5$ respectively, interconverting $R_8$ when hydrogen to $C_{1-6}$ alkyl, separating any enantiomers and forming a pharmaceutically acceptable salt or solvate.

The present invention also provides a process for the preparation of compounds of formula (Id), or a pharmaceutically acceptable salt thereof, which comprises acylating a compound of formula (IId):

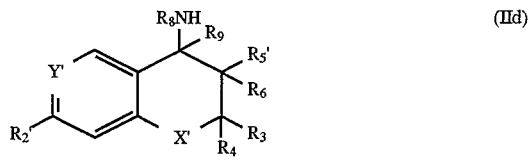
(IId)

in which X' is $NR_{10}'$ where $R_{10}'$ is hydrogen or $C_{1-6}$ alkyl or a group convertible thereto, Y', $R_2'$ and $R_5$ are Y, $R_2$ and $R_5$ respectively as defined in formula (I) or groups convertible thereto and $R_3$, $R_4$, $R_6$, $R_8$ and $R_9$ are as defined in formula (I), the $R_8$NH group being trans to the $R_5'$ group, with an acylating agent of formula (IIIb):

$R_7COL_1$  (IIIb)

where $R_7$ is as defined in formula (I) and $L_1$ is a leaving group, thereafter optionally or as necessary and in any appropriate order converting any Y', $R_{10}'$, $R_2'$ or $R_5'$ group to Y, $R_{10}$, $R_2$ or $R_5$ respectively, interconverting $R_8$ when hydrogen to $C_{1-6}$ alkyl, separating any enantiomers and forming a pharmaceutically acceptable salt or solvate.

Examples of suitable leaving groups $L_1$ include those mentioned in the above-mentioned patents, in particular EP-A-0 126 311 or are conventional in the art.

The reaction conditions which may be used to carry out the above reactions are as outlined or analogous to those described in the above-mentioned patents, in particular EP-A-0 126 311.

In particular, the leaving group ($L_1$) is a group that is displaceable by a primary or secondary amino nucleophile. Examples of such a group include $C_{1-4}$ alkylcarbonyloxy and halogen, such as chloro and bromo. When the leaving group ($L_1$) is any of these examples, the acylating agent of formula (IIIa) or (IIIb) is either an acid anhydride or an acid halide. When it is an acid anhydride, it is, preferably, a mixed anhydride, which may be prepared in situ from an aromatic or heteroaromatic carboxylic acid and an alkyl chlorocarbonate, such as ethyl chloroformate.

When the acylating agent of formula (IIIa) or (IIIb) is an acid anhydride, the acylation of the compound formula (IIa), (IIb), (IIc) or (IId) is, preferably, carded out using the anhydride as the solvent in the presence of an acid acceptor, such as sodium acetate.

When the acylating agent of formula (IIIa) or (IIIb) is an acid halide, the acylation of the compound of formula (IIa), (IIb), (IIc) or (IId), is, preferably, carried out in a non-aqueous medium, such as methylene chloride, in the presence of an acid acceptor, such as triethylamine, trimethylamine or pyridine.

Examples of suitable groups convertible to Y (or $R_1$), $R_2$ and $R_5$ include those described in the above-mentioned patents or are conventional in the art.

Interconversions of $R_8$ when hydrogen to $C_{1-6}$ alkyl may be carded out using conventional alkylation procedures for example using an alkylhalide in the presence of a base.

It should be appreciated that racemates for formula (I) may be resolved or enantiomerically purified compounds of formula (I) may be prepared using procedures conventional in the art and in particular using the procedures outlined in EP-0430631 and EP-0355584.

Suitably, the procedures outlined in or analogous to those described in Example 35 of the present specification may be used to prepare specific enantiomers of any compounds of formulae (I), (I'), (Ia), (Ib), (Ic) or (Id).

Compounds of formulae (I'), (IIa), (IIb), (IIc) and (IId) may be prepared from readily available starting materials using the procedures outlined or analogous to those described in the above-mentioned patents.

Compounds of formulae (IIIa) and (IIIb) are either commercially available or may be prepared according to conventional procedures known in the art of organic chemistry.

Novel compounds of formulae (I'), (IIa), (IIb), (IIc) and (IId) form an aspect of the present invention.

Compounds of formula (I) in which $R_5$ is hydroxy, $R_6$ is $C_{1-2}$ alkyl and $R_9$ is hydrogen may be prepared according to the procedures outlined in R. Gericke et al. *J. Med. Chem.* Vol. 34, p3074(1991).

The invention also provides a pharmaceutical composition comprising a compound of formula (I'), (Ia), (Ib), (Ic) or (d), or a pharmaceutically acceptable salt thereof, and a pharmaceutically acceptable carrier.

The invention also provides the use of a compound of formula (I'), (Ia), (Ib), (Ic) or (Id), or a pharmaceutically acceptable salt thereof, in the treatment and/or prophylaxis of anxiety and/or mania and/or depression and/or the effects associated with withdrawal from substances of abuse such as cocaine, nicotine, alcohol and benzadiazepines and/or disorders treatable and/or preventable with anti-convulsive agents, such as epilepsy.

The following examples and pharmacological test results illustrate the present invention:

The following compounds were prepared by methods analgous to those described in the abovementioned patents publications.

EXAMPLE 1 trans-6-Cyano-3,4-dihydro-2,2-dimethyl-4-(3-fluorobenzoylamino)2H-1-benzopyran-3-ol.
Mpt. 193°–194° C.

EXAMPLE 2 trans-6-Cyano-3,4-dihydro-2,2-dimethyl-4-(2-fluorobenzoylamino)2H-1-benzopyran-3-ol
Mpt. 163–5°

EXAMPLE 3 trans-6-Trifluoromethoxy-3,4-dihydro-2,2-dimethyl-4-(3-fluorobenzoylamino)2H-1-benzopyran-3-ol
Mpt. 127°–30° C.

EXAMPLE 4 trans-3,4-Dihydro-2,2-dimethyl-4-(4-fluorobenzoylamino)-2H-1-benzopyran-3-ol
Mpt. 174°–5° C.

EXAMPLE 5 trans-6-Cyano-3,4-dihydro-2,2-dimethyl-4-(4-fluorobenzoylamino)2H-1-benzopyran-3-ol.
Mpt. 229°–230° C. 3R, 4S isomer (compound B) Mpt. 224°–5° C.

EXAMPLE 6 trans-6-Chloro-3,4-dihydro-2,2-dimethyl-4-(4-fluorobenzoylamino)2H-1-benzopyran-3-ol.
Mpt. 177°–9° C.

EXAMPLE 7 trans-6-Trifluoromethyl-4-(4-fluorobenzoylamino)-3,4-dihydro-2,2-dimethyl-2H-1-benzopyran-3-ol.
Mpt. 185°–7° C.

EXAMPLE 8 trans-6-Cyano-4-(4-fluorobenzoylmethylamino)-3,4-dihydro-2,2-dimethyl-2H-1-benzopyran-3-ol.
Mpt. 230°–4° C.

EXAMPLE 9 trans-6-Ethylcarbonyl-3,4-dihydro-2,2-dimethyl-4-(4fluorobenzoylamino)2H-1-benzopyran-3-ol.
Mpt. 205°–207° C.

EXAMPLE 10 trans-6-Ethylcarbonyl-3,4-dihydro-2,2-dimethyl-4-(4-fluorobenzoylmethylamino)2H-1-benzopyran-3-ol.
Mpt. 210°–212° C.

EXAMPLE 11 trans-6-Acetyl-4-(4-fluorobenzoylmethylamino)-3,4-dihydro-2,2-dimethyl-2H-1-benzopyran-3-ol.
Mpt. 207°–8° C.

EXAMPLE 12 trans-6-Cyano-3,4-dihydro-4-(4-fluorobenzoylethylamino)-2,2-dimethyl-2H-1-benzopyran-3-ol
mp 172°–175° C.

EXAMPLE 13 trans-4-(4-Fluorobenzoylamino)-3,4-dihydro-2,2-dimethyl-7-nitro-2H-1-benzopyran-3-ol
mp 231°–233° C.

EXAMPLE 14 trans-4-(4-Fluorobenzoylamino)-3,4-dihydro-2,2,6-trimethyl-2H-1-benzopyran-3-ol
mp 185°–186° C.

EXAMPLE 15 trans-6-Ethyl-4-(4-fluorobenzoylamino)-3,4-dihydro-2,2-dimethyl-2H-1-benzopyran-3-ol
mp 235°–237° C.

EXAMPLE 16 trans-6-Ethyl-4-(4-fluorobenzoylethylamino)-3,4-dihydro-2,2-dimethyl-2H-1-benzopyran-3-ol
mp 175° C.

EXAMPLE 17 trans-4-(4-Fluorobenzoylamino)-3,4-dihydro-2,2-dimethyl-6-isopropyl-2H-1-benzopyran-3-ol
mp 235°–236° C.

EXAMPLE 18 trans-6-Acetyl-4-(4-fluorobenzoylamino)-3,4-dihydro-2,2-dimethyl-2H-1-benzopyran-3-ol
mp 203° C.

EXAMPLE 19 trans-6-Acetyl-4R-(4-fluorobenzoylamino)-3,4-dihydro-2,2-dimethyl-2H-1-benzopyran-3S-ol
mp 162°–163° C.

EXAMPLE 20 trans-6-Acetyl-4S-(4-fluorobenzoylamino)-3,4-dihydro-2,2-dimethyl-2H-1-benzopyran-3R-ol
mp 164° C.

EXAMPLE 21 trans-6-Cyano-4S-(3-fluorobenzoylamino)-3,4-dihydro-2,2-dimethyl-2H-1-benzopyran-3R-ol
mp 221° C.

EXAMPLE 22 trans-6-Cyano-4R-(3-fluorobenzoylamino)-3,4-dihydro-2,2-dimethyl-2H-1-benzopyran-3S-ol
mp 221° C.

EXAMPLE 23 trans-6-Ethyl-4-(4-fluorobenzoylmethylamino)-3,4-dihydro-2,2-dimethyl-2H-1-benzopyran-3-ol
mp 162°–164° C.

EXAMPLE 24 trans-6-Cyano-4S-(2-fluorobenzoylamino)-3,4-dihydro-2,2-dimethyl-2H-1-benzopyran-3R-ol
mp 163°–165° C.

EXAMPLE 25 trans-6-Cyano-4S-(4-fluorobenzoylamino)-3,4-dihydro-2,2-dimethyl-2H-1-benzopyran-3R-ol
mp 224°–225° C.

EXAMPLE 26 trans-6-Cyano-4-(4-fluorobenzoylamino)-3,4-dihydro-2,2,3-trimethyl-2H-1-benzopyran-3-ol
mp 218°–220° C.

EXAMPLE 27 trans-4-(4-Fluorobenzoylamino)-3,4-dihydro-2,2-dimethyl-6-nitro-2H-1-benzopyran-3-ol
mp 197°–198° C.

EXAMPLE 28 trans-6-Cyano-4S-(2,4-difluorobenzoylamino)-3,4-dihydro-2,2-dimethyl-2H-1-benzopyran-3R-ol
mp 175°–176° C.

EXAMPLE 29 trans-4-(4-Fluorobenzoylamino)-6-pentafluoroethyl-3,4-dihydro-2,2-dimethyl-2H-1-benzopyran-3-ol
mp 181° C.

EXAMPLE 30 trans-4-(4-Fluuorobenzoylamino)-3,4-dihydro-6-methoxycarbonyl-2,2-dimethyl-2H-1-benzopyran-3-ol
mp 198° C.

EXAMPLE 31 trans-6-Acetyl-4-(3-fluorobenzoylamino)-3,4-dihydro-2,2-dimethyl-2H-1-benzopyran-3-ol
mp 212° C.

EXAMPLE 32 trans-4-(4-Fluorobenzoylamino)-3,4-dihydro-2,2-dimethyl-6-phenylsulphonyl-2H-1-benzopyran-3-ol
mp 239°–240° C.

EXAMPLE 33 trans-4-(4-Fluorobenzoylamino)-3,4-dihydro-2,2-dimethyl-6-phenyl-2H-1-benzopyran-3-ol
mp 164°–165° C.

EXAMPLE 34 trans-6-Fluoro-4-(4-fluorobenzoylamino)-3,4-dihydro-2,2-dimethyl-2H-1-benzopyran-3-ol
mp 164°–165° C.

EXAMPLE 35 trans-6-Ethyl-4S-(4-fluorobenzoylamino)-3,4-dihydro-2,2-dimethyl-2H-1-benzopyran-3R-ol (-)-Mandelic acid was used to resolve the residue from resolution of trans-4-amino-6-ethyl-2,2-dimethyl-chroman-3-ol (to give the 3S, 4R enantiomer —as described in EPA 412 760) under standard resolving conditions using acetone as recrystallisation solvent. This furnished trans-4S-amino-6-ethyl-2,2-dimethylchroman-3R-ol D-mandelate.

The 4S, 3R-aminoalcohol mandelate (4.0 g) was dissolved in dichloromethane (250 ml) and triethylamine (3.34 ml) and cooled in an ice bath. To this stirred solution was added 4-fluorobenzoyl chloride (1.7 g) dropwise. On completion of addition the reaction mixture was allowed to attain room temperature and was stirred overnight. The solvent was evaporated and the residue was taken up in ethyl acetate (150 ml). This solution was washed with 5% sodium bicarbonate solution, and brine, and dried over anhydrous magnesium sulphate. Filtration and evaporation and recrystallisation of the residue from Ethyl acetate-hexane gave the title compound of example 35. mp 132°–136° C. $\alpha D/20$+ 69.1° (methanol, c=1.0).

| NMR(CDCL3)δ | 1.21 (3H, t, J = 8 Hz) |
| --- | --- |
| | 1.28 (3H, s) |
| | 1.49 (3H, s) |
| | 2.88 (2H, q, J = 8 Hz) |
| | 3.76 (1H, d, J = 9 Hz) |
| | 4.46 (1H, broad s) |
| | 5.21 (1H, t, J = 9, 8 Hz) |
| | 6.41 (1H, d, J = 8 Hz) |
| | 6.80 (1H, d, J = 9 Hz) |
| | 7.07 (2H, irregular m) |
| | 7.17 (2H, t, J = 9 Hz) |
| | 7.74 (2H, m) |

EXAMPLE 36 trans-4R-(4-Fluorobenzoylamino)-3,4-dihydro-6-(1-hydroxyethyl)-2,2-dimethyl-2H-1-benzopyran-3S-ol
mp 132°–133° C.

EXAMPLE 37 trans-4S-(4-Fluorobenzoylamino)-3,4-dihydro-6-(1-hydroxyethyl)-2,2-dimethyl-2H-1-benzopyran-3R-ol
mp 133°–134° C.

EXAMPLE 38 trans-4-(2-Fluorobenzoylamino)-3,4-dihydro-2,2-dimethyl-2H-pyrano[3,2-c]pyridin-3-ol
mp 254° C.

EXAMPLE 39 trans-4-(3-Fluorobenzoylamino)-3,4-dihydro-2,2-dimethyl-2H-pyrano[3,2c]pyridin-3-ol
mp 259°–261° C.

EXAMPLE 40 trans-4-(4-Fluuorobenzoylamino)-3,4-dihydro-2,2-dimethyl-2H-pyrano[3,2-c]pyridin-3-ol
mp 254°–255° C.

EXAMPLE 41 trans-6-Cyano-4-(3,4-difluorbenzoyl-methylamino)-3,4-dihydro-2,2-dimethyl-2H-1-benzopyran-3-ol
mp 199°–200° C.

EXAMPLE 42 trans-4-(4-fluorobenzoyl-methylamino)-6-trifluoromethyl-3,4-dihydro-2,2-dimethyl-2H-1-benzopyran-3-ol
mp 196°–197° C.

EXAMPLE 43 trans-4-(4-fluorobenzoyl-methylamino)-3,4-dihydro-2,2-dimethyl-2H-1-benzopyran-3-ol
mp 160°–161° C.

EXAMPLE 44 trans-6-cyano-4S-(3,4-difluorobenzoylamino)-3,4-dihydro-2,2-dimethyl-2H-1-benzopyran-3R-ol
mp 227° C.

EXAMPLE 45 trans-6-Cyano-4-(4-fluorobenzoylamino)-2,2-dimethyl-1,2,3,4-tetrahydroquinolin-3-ol
mp 244°–248° C.

EXAMPLE 46 trans-6-t-Butyl-4-(4-fluorobenzoylamino)-3,4-dihydro-2,2-dimethyl-2H-1-benzopyran-3-ol
mp 163°–166° C.

EXAMPLE 47 trans-4-(4-Fluorobenzoylamino)-3,4-dihydro-6-iodo-2,2-dimethyl-2H-1-benzopyran-3-ol
mp 204°–205° C.

EXAMPLE 48 trans-4-(4-Fluuorobenzoylamino)-3,4-dihydro-2,2-dimethyl-6-cyclopentyl-2H-1-benzopyran-3-ol
mp 173°–174° C.

EXAMPLE 49 trans-6-Aminocarbonylmethyl-4-(4-fluorobenzoylamino)-3,4-dihydro-2,2-dimethyl-2H-1-benzopyran-3-ol
mp 190° C.

EXAMPLE 50 trans-4-(4-Fluorobenzoylamino)-3,4-dihydro-6-methoxy-2,2-dimethyl-2H-1-benzopyran-3-ol
mp 155°–156° C.

PHARMACOLOGICAL DATA

1. Geller-Seifter Procedure

Potential anxiolytic properties are evaluated using the Geller-Seifter procedure based on that originally described by Geller and Seifter, (1960) Psychopharmacologia, 1, 482–492. This procedure has been shown to be selective for drugs with anxiolytic properties (Cook and Sepinwall, (1975) "Mechanism of Action of Benzodiazepines" ed. Costa, E. and Greengard, P., Raven Press, New York, pp. 1–28).

Rats are trained on a variable interval 30 sec schedule (VI30) to press a lever in order to obtain food reward. The 5 min sessions of the VI30 schedule alternate with 2–5 min of a schedule (FR5) in which every 5th lever press is followed by presentation of a food pellet paired with a 0.5 sec mild footshock. The total study lasts approximately 30 mins. Rats typically respond with high rates of lever pressing under the VI30 schedule and low response rates under the FR5 'conflict' session. Anxiolytic drugs increase the suppressed response rates of rats in a 'conflict' session.

Drugs are administered intraperitoneally or orally to groups of 3–8 rats 30 to 60 mins before testing.

The results are expressed as the percentage increase in the square root of the total number of lever presses in the FR5 'conflict' session. Square root transformation is necessary to normalise the data for statistical analysis using parametric methods.

The compound of Example 4 showed a significant increase in responding in the 'conflict' session at a dose of 10 mg/kg p.o.

2. Mes Test

The maximal electroshock seizure (MES) test in rodents is one of the most widely used models of human grand mal epilepsy[1]. In this model, anticonvulsant agents elevate the threshold to electrically-induced seizures whilst proconvulsants lower the seizure threshold.

Method

Mice (male, Charles River, U.K. CD-1 strain, 25–30 g) are randomly assigned to groups of 10–20 and dosed orally or intraperitoneally at a dose volume of 10 ml/kg with various doses of compound (1–100 mg/kg) or vehicle. Mice are then subjected at 30 or 60 min post dose to a variable voltage electroshock (0.1 sec., 50 Hz, sine wave form) via a buccal and a subcutaneous electrode. The mean voltage and standard error required to induce a tonic seizure in 50% ($CV_{50}$) of the mice in the group is determined by the 'up and down' method of Dixon and Mood (1948)[2]. Statistical comparisons between vehicle-and drug-treated groups are made using the method of Litchfield and Wilcoxon (1949)[3].

In control animals the $CV_{50}$ is usually 40–50 V. Hence the first animal in the control group is subjected to a voltage of 45 V. If a tonic seizure does not ensue, the voltage is increased for a subsequent mouse. If a tonic convulsion does occur, then the voltage is decreased, and so on until all the animals in the group have been tested.

The percentage increase or decrease in $CV_{50}$ for each group compared to the control is calculated.

Studies are carried out using a Heathkit shock generator with totally variable control of shock level from 0 to 200 V and voltage steps of 5 V are used.

Drugs are suspended in 1% methyl cellulose.

Reference

1. Swinyard, E. A. (1972). Electrically-induced convulsions. In: Experimental Models of Epilepsy ed. Purpura, D. P. et al., 433–458, Raven Press, New York.

2. Dixon, W. J. and Mood, A. M. (1948). J. Amer. Stat. Assn., 43, 109–126.

3. Litchfield, J. T. and Wilcoxon, F. (1949). J. Pharmacol. Exp. Ther. 96, 99–113.

Results

Compounds of Examples 1–3, 5, 7, 8, 18, 20, 21, 25, 30, 31, 35 and 37 and compound X showed a significant increase in $CV_{50}$ at a dose of 10 mg/kg p.o.

3. X-Maze

Introduction

The X-maze test of anxiety (Handley and Mithani, 1984) examines the exploratory response of naive rats in an environment which offers both anxiogenic (open arms) and relatively non-anxiogenic (closed arms) areas. A selective increase in exploration of the open arms following drug pretreatment is therefore postulated to indicate anxiolytic effects.

Method

The X-maze was raised 70 cm above the floor and consisted of two enclosed arms 45 cm (long)×15 cm (wide)

×10 cm (high) and two open arms 45×10 ×1 cm arranged such that the two arms of each type were opposite each other. Both arm types were marked into two equal sections. Rats were placed onto the centre of the X-maze and observed for a period of 10 minutes during which time the following parameters were recorded: 1) the number of entries onto, and the time spent on, (a) open arms, (b) closed arms, (c) end of open arms and (d) end of closed arms. 2) the number of sections crossed. The fear-drive evoked in the open arms exceeds that in the enclosed arms and rats typically show a clear preference for the enclosed arms. Anxiolytic drugs increase the number of entries made onto, and the time spent on, the outer half of the open arms, and also the percentage of entries made onto, and the time spent on, the whole of the open arms. These four measures of anxiety, and also the total number of sections traversed, were calculated for each animal. Drugs are administered intraperitoneally or orally to groups of 6 to 12 rats 30 to 60 mins before testing. Statistical comparisons between vehicle-and drug-treated groups were made using a Mann-Whitney 'U' test (two tailed).

S. L. Handley and S. Mithani, Arch. Pharmacol., 1984 327 1–5

Results

The compound of Example 21, caused a significant increase in open arm entries at a dose of 30 mg/kg p.o.

We claim:

1. The method of treatment of anxiety, mania, depression or the effects associated with withdrawal from substances of abuse, or disorders treatable or preventable with anti-convulsive agents, comprising administering to the sufferer in need thereof an effective amount of a compound of formula (I), or a pharmaceutically acceptable salt thereof:

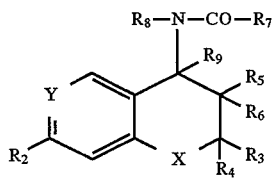

wherein:

Y is C—$R_1$ where:

$R_1$ is cyano, methoxy, trifluoromethoxy, chloro, trifluoromethyl, ethylcarbonyl, acetyl, hydrogen, methyl, ethyl, iso-propyl, tertiary-butyl, nitro, $C_2F_5$, methoxycarbonyl, phenylsulphonyl, phenyl, fluoro, iodo, cyclopentyl, aminocarbonylmethyl or 1-hydroxyethyl;

$R_2$ is hydrogen;

$R_3$ and $R_4$ are independently methyl;

$R_5$ is hydroxy and $R_6$ is hydrogen or $C_{1-2}$ alkyl and $R_9$ is hydrogen;

$R_7$ is fluorophenyl;

$R_8$ is hydrogen or $C_{1-6}$ alkyl;

the $R_8$—N—CO—$R_7$ group being trans to the $R_5$ group;

and X is oxygen.

2. The method of prophylaxis of anxiety, mania, depression or the effects associated with withdrawal from substances of abuse, or disorders treatable or preventable with anti-convulsive agents, comprising administering to the sufferer in need thereof an prophylactic amount of a compound of formula (I), or a pharmaceutically acceptable salt thereof;

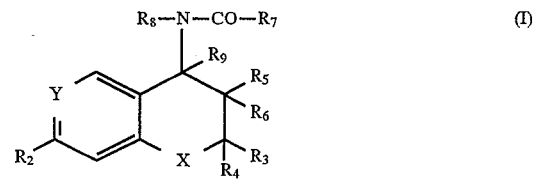

wherein:

Y is C—$R_1$ where:

$R_1$ is cyano, methoxy, trifluoromethoxy, chloro, trifluoromethyl, ethylcarbonyl, acetyl, hydrogen, methyl, ethyl, iso-propyl, tertiary-butyl, nitro, $C_2F_5$, methoxycarbonyl, phenylsulphonyl, phenyl, fluoro, iodo, cyclopentyl, aminocarbonylmethyl or 1-hydroxyethyl;

$R_2$ is hydrogen $R_3$ and $R_4$ are methyl;

$R_5$ is hydroxy and $R_6$ is hydrogen or $C_{1-2}$ alkyl and $R_9$ is hydrogen;

$R_7$ is fluorophenyl;

$R_8$ is hydrogen or $C_{1-6}$ alkyl;

the $R_8$—N—CO—$R_7$ group being trans to the $R_5$ group;

and X is oxygen.

3. A method of treatment according to claim 1 wherein the compound of formula (I) is trans-6-Acetyl-4S-(4-fluorobenzoylamino)-3,4-dihydro-2,2-dimethyl-2H-1-benzopyran-3R-ol.

4. A method of prophylaxis according to claim 2 wherein the compound of formula (I) is trans-6-Acetyl-4S-(4-fluorobenzoylamino)-3,4-dihydro-2,2-dimethyl-2H-1-benzopyran-3 R-ol.

5. A method of treatment according to claim 1 wherein the disorder is Epilepsy.

6. A method of prophylaxis according to claim 2 wherein the disorder is epilepsy.

7. A method of treatment according to claim 5 wherein the compound of formula (I) is trans-6-acetyl-4S-(4-fluorobenzoylamino)-3,4-dihydro-2,2-dimethyl-2H-1-benzopyran-3R-ol.

8. A method of prophylaxis according to claim 6 wherein the compound of formula (I) is trans-6-acetyl-4S-(4-fluorobenzoylamino)-3,4-dihydro-2,2-dimethyl-2H-1-benzopyran-3R-ol.

* * * * *